US010028812B2

(12) United States Patent
Shabat

(10) Patent No.: US 10,028,812 B2
(45) Date of Patent: Jul. 24, 2018

(54) GIRTH DEVICE AND METHOD FOR CONTROLLING URINARY INCONTINENCE

(71) Applicant: URICON LTD, Natzrat-Elit (IL)

(72) Inventor: Roni Shabat, Kfar Yeheskel (IL)

( * ) Notice: Subject to any disclaimer, the term of this patent is extended or adjusted under 35 U.S.C. 154(b) by 327 days.

(21) Appl. No.: 14/421,166

(22) PCT Filed: Aug. 12, 2013

(86) PCT No.: PCT/IL2013/050682
§ 371 (c)(1),
(2) Date: Feb. 12, 2015

(87) PCT Pub. No.: WO2014/027344
PCT Pub. Date: Feb. 20, 2014

(65) Prior Publication Data
US 2015/0230904 A1  Aug. 20, 2015

Related U.S. Application Data

(60) Provisional application No. 61/682,262, filed on Aug. 12, 2012.

(51) Int. Cl.
*A61F 2/00* (2006.01)

(52) U.S. Cl.
CPC .................. *A61F 2/004* (2013.01)

(58) Field of Classification Search
CPC .............. A61F 2/004; A61F 2230/0013; A61F 2250/0003; A61F 2250/001; A61F 2250/0013; A61B 2017/00805; A61B 17/1227; A61B 2017/00557

USPC ...................................................... 600/29–31
See application file for complete search history.

(56) References Cited

U.S. PATENT DOCUMENTS

| 3,744,063 A | * | 7/1973 | McWhorter | A61F 2/004 |
| | | | | 128/DIG. 25 |
| 3,815,576 A | | 6/1974 | Balaban | |
| 4,056,095 A | | 11/1977 | Rey et al. | |
| 4,178,915 A | | 12/1979 | Szinicz et al. | |
| 4,222,377 A | * | 9/1980 | Burton | A61F 2/004 |
| | | | | 128/DIG. 25 |

(Continued)

FOREIGN PATENT DOCUMENTS

| EP | 2 243 446 | 10/2010 |
| FR | 2 331 995 | 6/1977 |
| WO | 2012/141923 | 10/2012 |

*Primary Examiner* — Navin Natnithithadha
*Assistant Examiner* — Sunita Reddy
(74) *Attorney, Agent, or Firm* — The Law Office of Joseph L. Felber

(57) ABSTRACT

An implantable girth control device for controlling urinary incontinence by placing the device around the urethra. The device comprising an adjustable resilient circumferential collar comprising a strap for embracing the urethra, the strap having two inflatable/deflatable expandable members, the first expandable member is a fluid filled expandable member that is affixed to an inner portion of the strap and in contact with the urethra, the second expandable member is affixed to an outer portion of the strap and is in fluid communication with the first expandable member over a valve. The valve is configured facilitate fluid transfer between the two members in response to changes in urethral pressure and to control a collar pressure applied by the device onto the urethra.

26 Claims, 14 Drawing Sheets

(56) References Cited

U.S. PATENT DOCUMENTS

| | | | |
|---|---|---|---|
| 4,256,093 A | | 3/1981 | Helms et al. |
| 4,412,530 A | * | 11/1983 | Burton .................... A61F 2/004 |
| | | | 128/DIG. 25 |
| 4,556,050 A | * | 12/1985 | Hodgson ................ A61F 2/004 |
| | | | 128/DIG. 25 |
| 4,878,889 A | * | 11/1989 | Polyak .................... A61F 2/004 |
| | | | 128/DIG. 25 |
| 4,909,785 A | * | 3/1990 | Burton .................. A61F 2/0027 |
| | | | 604/544 |
| 4,994,020 A | * | 2/1991 | Polyak .................... A61F 2/004 |
| | | | 128/DIG. 25 |
| 5,518,504 A | * | 5/1996 | Polyak .................. A61F 2/0036 |
| | | | 128/DIG. 25 |
| 2007/0167962 A1 | * | 7/2007 | Gannoe ............ A61B 17/00234 |
| | | | 606/153 |
| 2007/0249893 A1 | | 10/2007 | Krumme |
| 2009/0012350 A1 | * | 1/2009 | Tihon .................. A61B 17/282 |
| | | | 600/30 |
| 2009/0018385 A1 | * | 1/2009 | Trubiano .............. A61F 2/0036 |
| | | | 600/30 |
| 2009/0306460 A1 | * | 12/2009 | Stephens ........... A61N 1/36007 |
| | | | 600/30 |
| 2010/0160716 A1 | * | 6/2010 | Snow ...................... A61F 2/004 |
| | | | 600/31 |
| 2012/0157759 A1 | * | 6/2012 | Wirbisky ................ A61F 2/004 |
| | | | 600/31 |

\* cited by examiner

GIRTH DEVICE AND METHOD FOR CONTROLLING URINARY INCONTINENCE

This Application is a national phase of, and claims priority from, PCT Application No. PCT/IL2013/050682, filed on Aug. 12, 2013, which claims priority from U.S. Provisional Application No. 61/682,262, filed Aug. 12, 2012, which is hereby incorporated by reference as if fully set forth herein.

FIELD OF THE INVENTION

This invention concerns a girth device and method for the treatment of stress urinary incontinence, and more particularly to minimally invasive implantation of a collar device having expandable members configured for achieving the best effect and treatment.

BACKGROUND

Stress urinary incontinence (SUI), also known as effort incontinence, is a well known phenomena. SUI is due essentially to insufficient strength of the pelvic floor muscles. SUI is the loss of small amounts of urine associated with coughing, laughing, sneezing, exercising or other movements that increase intra-abdominal pressure and thus increase pressure on the bladder. The urethra is supported by fascia of the pelvic floor. If this support is insufficient, the urethra can move downward at times of increased abdominal pressure, allowing urine to pass.

Various attempts have been made to artificially produce urinary continence. Early attempts to prevent male incontinence involved externally clamping the penis; but, pressure sufficient to stop urinary flow tends also to compromise circulation, causing pain, skin alteration and thrombosis. An analogous application for women, compressing the urethra between the vaginal wall and the pubic bone, shares these disadvantages.

U.S. Pat. No. 4,256,093 issued to Curtis Helms et al teaches the use of a fluid filled urethra collar which is contracted by manually squeezing a bulb implanted in the scrotum.

U.S. Pat. No. 3,815,576 issued to Donald R. Balaban teaches the use of a fluid filled flexible container implanted in the patient which is squeezed manually to actuate a piston-cylinder in a U-shaped clamp. Similarly, U.S. Pat. No. 4,056,095 issued to Pierre Rey et al and U.S. Pat. No. 4,178,915 issued to Gerhard Sznicz et al teach the use of a fluid filled artificial sphincter which is actuated by pressing on the subcutaneously implanted membrane. These references share the disadvantage of having no control over the pressure exerted by the device on the urethra once the apparatus is implanted. It therefore remains a long felt and unmet need to provide novel means and methods for treating and controlling urinary incontinence pressure.

SUMMARY

It is an object of the present invention to disclose an implantable girth device for controlling urinary incontinence comprising: an adjustable resilient circumferential collar 1 for surrounding the urethra; said collar comprises:
(i) a strap 10 for snugly embracing said urethra, said strap comprising an inner surface 5 and an outer surface 2, (ii) a first inflatable/deflatable expandable flexible elastic member 3 for limiting expansion of the lumen of said urethra affixed to portion of said inner surface 5 of said collar, (iii) a second inflatable/deflatable expandable non elastic reservoir 4 affixed to portion of said outer surface 3 of said collar 1; said expandable reservoir comprises a fluid, and (iv) a valve for fluidly communicating said first inflatable/deflatable expandable flexible elastic 4 member with said second inflatable/deflatable expandable non elastic reservoir 4. The collar pressure upon said urethra is increased or decreased with sensed urethra pressure such that when urethral pressure is exerted against said strap said first expandable member affixed to said strap is deflated by transferring said fluid through said valve to said second expandable reservoir resulting in continence such that urine remains in said urethra for about 1.5 seconds; further wherein when urethral pressure decreases, said second expandable reservoir transfers said fluid to said first expandable member such that both said second expandable reservoir and said first expandable member are approximately resuming their original shape.

It is another object of the present invention to provide the girth device as defined above, wherein said collar pressure upon said urethra is maintained between about 5 cms $H_2O$ and about 20 cms $H_2O$ for about 1.5 secs.

It is another object of the present invention to provide the girth device as defined above, wherein said collar is limiting the expansion of said urethral diameter beyond a predetermined diameter during intermittent abrupt high bladder and urethral pressure episodes of duration of about 0.5 secs.

It is one object of the present invention to provide implantable girth device for controlling urinary incontinence comprising: an adjustable resilient circumferential collar 1 for surrounding the urethra; said collar comprises:
(i) a strap 6 for snugly embracing said urethra, said strap comprising an inner surface 5 and an outer surface 2, (ii) a first inflatable/deflatable expandable flexible elastic member 3 for limiting expansion of the lumen of said urethra affixed to portion of said inner surface 5 of said collar, (iii) a second inflatable/deflatable expandable non elastic reservoir 4 affixed to portion of said outer surface 2 of said collar 1; said expandable reservoir comprises a fluid, and (iv) a valve for fluidly communicating said first inflatable/deflatable expandable flexible elastic 3 member with said second inflatable/deflatable expandable non elastic reservoir 4. The valve is configured to restrict fluid transfer between said expandable first inflatable/deflatable expandable flexible elastic member and second inflatable/deflatable expandable non elastic reservoir such that collar pressure upon said urethra is maintained between about 5 cms $H_2O$ and about 20 cms $H_2O$ for a about 1.5 secs. thereby limiting expansion of said urethral diameter beyond a predetermined diameter during intermittent abrupt high bladder and urethral pressure episodes of duration of about 0.5 secs.

It is one object of the present invention to provide an orifice for fluidly communicating a first inflatable/deflatable expandable flexible elastic member with a second inflatable/deflatable expandable non elastic reservoir of an implantable girth device; said girth device is for controlling urinary incontinence. The orifice is a valve configured to restrict fluid transfer between said expandable first inflatable/deflatable expandable flexible elastic member and second inflatable/deflatable expandable non elastic reservoir such that girth device pressure upon the urethra is maintained between about 5 cms $H_2O$ and about 20 cms $H_2O$ for about 1.5 secs. thereby limiting expansion of said urethral diameter beyond a predetermined diameter during intermittent abrupt high bladder and urethral pressure episodes of duration of about 0.5 secs.

It is another object of the present invention to provide the orifice as defined above, wherein said orifice structure is selected from a group consisting of valve, tube-like, passage like, orifice annular, pipe, needle valve, hole, nozzle or any structure designed to control the direction or characteristics of a fluid flow.

It is another object of the present invention to provide the orifice as defined above, wherein said intermittent abrupt high bladder and urethral pressure episodes of duration of about 0.5 secs is about 150 cms. of $H_2O$.

It is another object of the present invention to provide the girth device as defined above, wherein said collar is adapted for changing both the urethra and bladder pressure factors.

It is another object of the present invention to provide the girth and the orifice devices as defined above, wherein said first expandable member can be filled with fluid, or the fluid pressure can be reset after implantation without necessitating a surgical procedure.

It is another object of the present invention to provide the girth and the orifice devices as defined above, wherein said first expandable member is biocompatible member made of an elastic material such as nylon.

It is another object of the present invention to provide the girth and the orifice devices as defined above, wherein said first expandable member may be filled with additional fluid such that it could be adjusted to the patient urethra pressure.

It is another object of the present invention to provide the girth and the orifice devices as defined above, wherein said second expandable member is a biocompatible member made of un elastic material with the ability to be expanded by a fluid.

It is another object of the present invention to provide the girth device as defined above, wherein said collar may be of variety of lengths to accommodate different urethra size.

It is another object of the present invention to provide the girth device as defined above, wherein said strap has a belt like structure and mechanism such that it may be adjusted to different urethra size.

It is another object of the present invention to provide the girth device as defined above, wherein said strap is made of biocompatible material allowing said device to integrate with the body tissue.

It is another object of the present invention to provide the girth device as defined above, wherein said collar has an open configuration and a close configuration.

It is another object of the present invention to provide the girth device as defined above, wherein said strap has a resilient circumferential shape having a buckle for opening and closing said strap when needed.

It is another object of the present invention to provide the girth device as defined above, wherein said collar balance between urethral closure and detrusor muscle activity.

It is another object of the present invention to provide the girth device as defined above, wherein said fluid is selected from a group consisting of viscous fluid or water based fluid.

It is another object of the present invention to provide the girth and the orifice devices as defined above, wherein said valve has a predetermined diameter and structure which allows fluid flow passage there through.

It is another object of the present invention to provide the girth and the orifice devices as defined above, wherein transferring said fluid from first expandable member to second expandable reservoir takes 1.5 seconds, allowing said collar to control the flow of urine by activating pressure on said urethra.

It is another object of the present invention to provide the girth and the orifice devices as defined above, wherein deflation of said first expandable member lower the pressure of said collar upon said urethra therefore resulting release of urine.

It is another object of the present invention to provide the girth and the orifice devices as defined above, wherein said valve has a tunnel structure for fluidly communicating of said first inflatable/deflatable expandable flexible elastic member with said second inflatable/deflatable expandable non elastic reservoir.

It is another object of the present invention to provide the girth and the orifice devices as defined above, wherein said collar comprises at least one broad strap portion and at least one narrow strap portion.

It is another object of the present invention to provide the girth and the orifice devices as defined above, wherein at least one portion of said strap has a mesh like structure.

It is still an object of the present invention to provide a method of controlling urinary incontinence comprising the steps of:

(a) providing an urethra implanted device for treating urinary incontinence comprising: (i) an adjustable resilient circumferential collar 10 for surrounding the urethra; said collar comprises: (b) a strap for snugly embracing said urethra, said strap comprising an inner surface and an outer surface, (b) a first inflatable/deflatable expandable flexible elastic member 3 for limiting expansion of the lumen of said urethra affixed to portion of said inner surface 2 of said collar, (c) a second inflatable/deflatable expandable non elastic reservoir 4 affixed to portion of said outer surface 1 of said collar 10; said expandable reservoir comprises a fluid, and, (d) a valve for fluidly communicating said first inflatable/deflatable expandable flexible elastic member with said second inflatable/deflatable expandable non elastic reservoir;

(b) placing said urethra implanted device upon said urethra, and (c) adjusting and securing said collar strap for surrounding said urethra. The collar pressure upon said urethra is increased or decreased with sensed urethra pressure such that when urethral pressure is exerted against said strap said first expandable member affixed to said strap is deflated by transferring said fluid through said valve to said second expandable reservoir resulting in continence such that urine remains in said bladder for about 1.5 seconds; further wherein when urethral pressure decreases, said second expandable reservoir transfers said fluid to said first expandable member such that both said second expandable reservoir and said first expandable member are approximately resuming their original shape.

It is still an object of the present invention to provide a method of controlling urinary incontinence comprising the steps of:

(a) providing an urethra implanted device for treating urinary incontinence comprising: (i) an adjustable resilient circumferential collar 10 for surrounding the urethra; said collar comprises: (a) a strap for snugly embracing said urethra, said strap comprising an inner surface and an outer surface, (b) a first inflatable/deflatable expandable flexible elastic member 3 for limiting expansion of the lumen of said urethra affixed to portion of said inner surface 2 of said collar, (c) a second inflatable/deflatable expandable non elastic reservoir 4 affixed to portion of said outer surface 1 of said collar 10; said expandable reservoir comprises a fluid, and, (d) a valve for fluidly communicating said first inflatable/deflatable expandable flexible elastic member with said second inflatable/deflatable expandable non elastic reservoir. The valve is configured to restrict fluid transfer between said expandable first inflatable/deflatable expandable flexible elastic 4 member and second inflatable/deflatable expandable non elastic reservoir 5 such that collar pressure upon said urethra is maintained between about 5 cms H$_2$O and about 20 cms H$_2$O for a about 1.5 secs. thereby limiting expansion of said urethral diameter beyond a predetermined diameter during intermittent abrupt high bladder and urethral pressure episodes of duration of about 0.5 secs. (b) placing said urethra implanted device upon said urethra; and (c) adjusting and securing said collar strap for surrounding said urethra.

It is an object of the present invention to provide the method as defined above, wherein said intermittent abrupt high bladder and urethral pressure episodes of duration of about 0.5 secs is about 150 cms. of H$_2$O.

It is an object of the present invention to provide the method as defined above, wherein said step of adjusting and securing said collar strap in a manner for occluding the flow of urine from said urethra when the urethra pressure rises.

It is an object of the present invention to provide the method as defined above, further comprises the step of closing said strap around the urethra in a generally circular shape using a buckle.

It is an object of the present invention to provide the method as defined above, wherein said collar has an open configuration and a close configuration.

It is an object of the present invention to provide the method as defined above, wherein said inserting said urethra implanted device in been performed in a manner such as an open position of said strap or a closed position of said strap It is an object of the present invention to provide the method as defined above, wherein said collar is adapted for changing both the urethra and bladder pressure factors.

It is an object of the present invention to provide the method as defined above, wherein said first expendable member is filled with fluid, or the fluid pressure can be reset, after implantation without necessitating a surgical procedure.

It is an object of the present invention to provide the method as defined above, wherein said first expendable member is biocompatible member made of an elastic material such as nylon.

It is an object of the present invention to provide the method as defined above, wherein said first expendable member may be filled with additional fluid such that it could be adjusted to the patient urethra pressure.

It is an object of the present invention to provide the method as defined above, wherein said second expendable member is biocompatible member made of un elastic material It is an object of the present invention to provide the method as defined above, wherein said collar may be of different sizes to accommodate different urethra size.

It is an object of the present invention to provide the method as defined above, wherein said strap has a belt like structure such that it may be adjusted to different urethra size.

It is an object of the present invention to provide the method as defined above, wherein said strap is made of biocompatible material allowing said device to integrate with the body tissue.

It is an object of the present invention to provide the method as defined above, wherein said strap has a resilient circumferential shape having a buckle for opening and closing said strap.

It is an object of the present invention to provide the method as defined above, wherein said collar balance between urethral closure and detrusor muscle activity It is an object of the present invention to provide the method as defined above, wherein said fluid is selected from a group consisting of viscous or water based fluids.

It is an object of the present invention to provide the method as defined above, wherein said valve for fluidly communicating has a diameter such that fluid transfer between said expandable first inflatable/deflatable expandable flexible elastic 4 member and said second inflatable/deflatable expandable non elastic reservoir takes about 1.5 secs It is an object of the present invention to provide the method as defined above, wherein transferring said fluid from first expandable member to second expandable reservoir takes 1.5 seconds, allowing said collar to control the flow of urine by activating pressure on said urethra.

It is an object of the present invention to provide the method as defined above, wherein deflation of said first expandable member lower the pressure of said collar upon said urethra therefore resulting release of urine.

It is an object of the present invention to provide the method as defined above, wherein said valve has an inner lumen shape for fluidly communicating of said first inflatable/deflatable expandable flexible elastic member with said second inflatable/deflatable expandable non elastic reservoir;

It is an object of the present invention to provide the method as defined above, wherein said collar comprises a broad strap portion and a narrow strap portion It is an object of the present invention to provide the method as defined above, wherein at least one portion of said strap has a mesh like structure.

BRIEF DESCRIPTION

In order to understand the invention and to see how it may be implemented in practice, a few preferred embodiments will now be described, by way of non-limiting example only, with reference to be accompanying drawings, in which:

FIG. 1*a-b* presents a prior art graph of the Valsalva leak point pressure study, in accordance with a preferred embodiment of the present invention; and FIG. 2 presents a prior art graph of the urethral pressure profile measurement, in accordance with a preferred embodiment of the present invention.

FIG. 3 presents the girth device for controlling urinary incontinence, in accordance with a preferred embodiment of the present invention;

FIG. 4*a-b* is a top view of the girth device, in accordance with a preferred embodiment of the present invention;

Figure 7A:
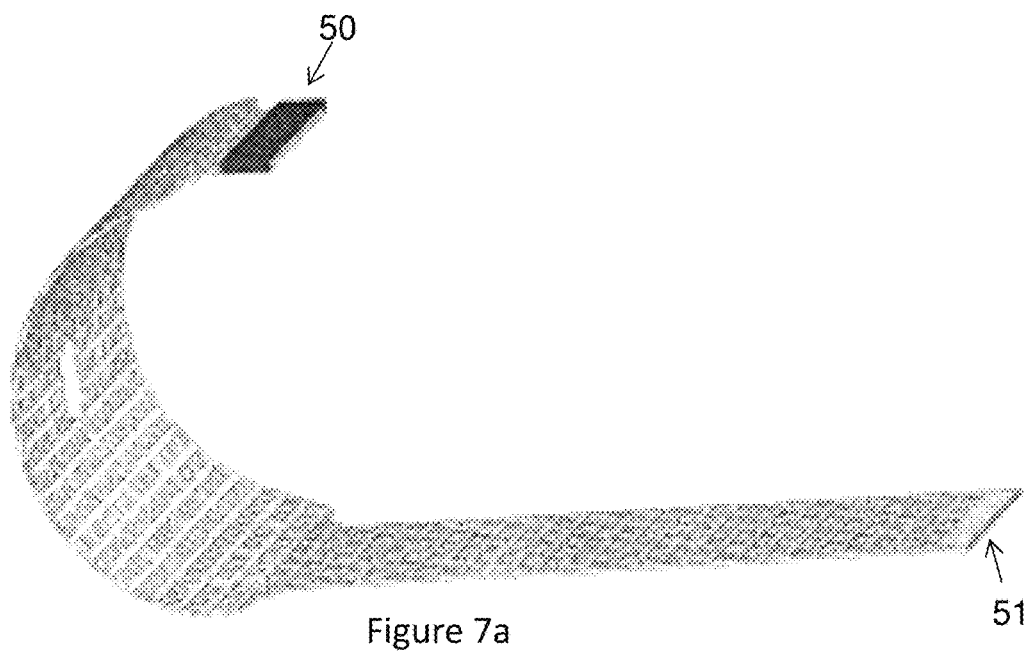
Figure 7B:
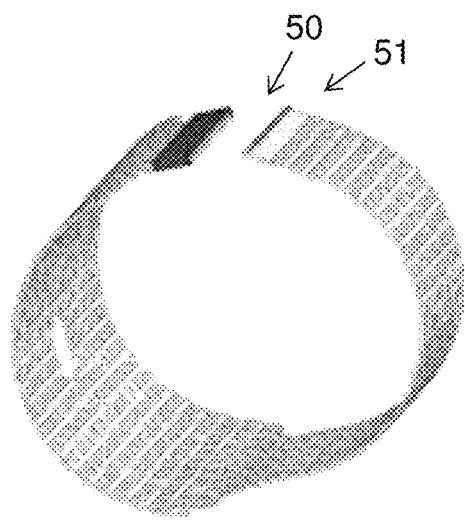
Figure 7C:
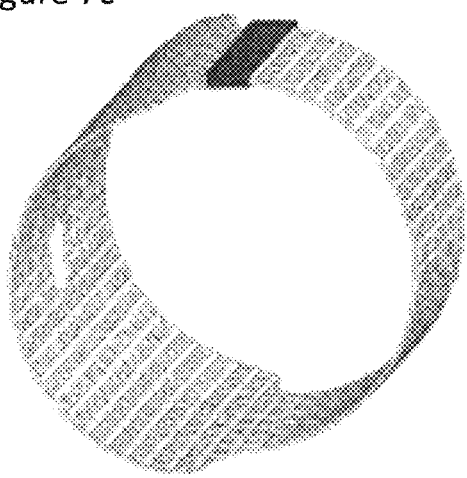
Figure 8A:
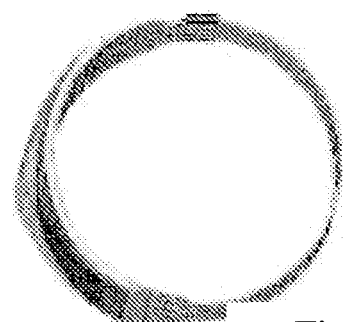
Figure 8A:
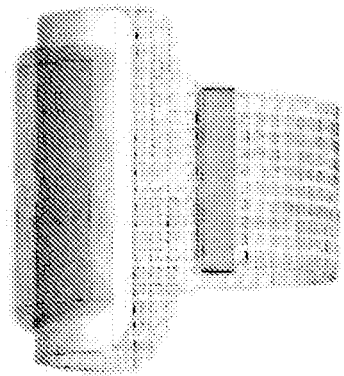
Figure 8C:
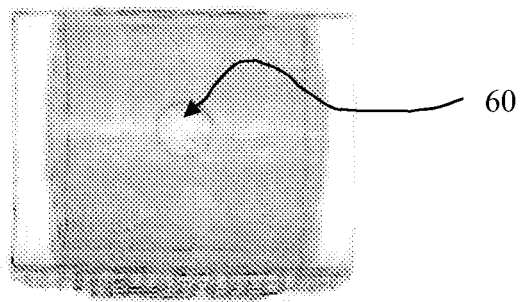
Figure 9:
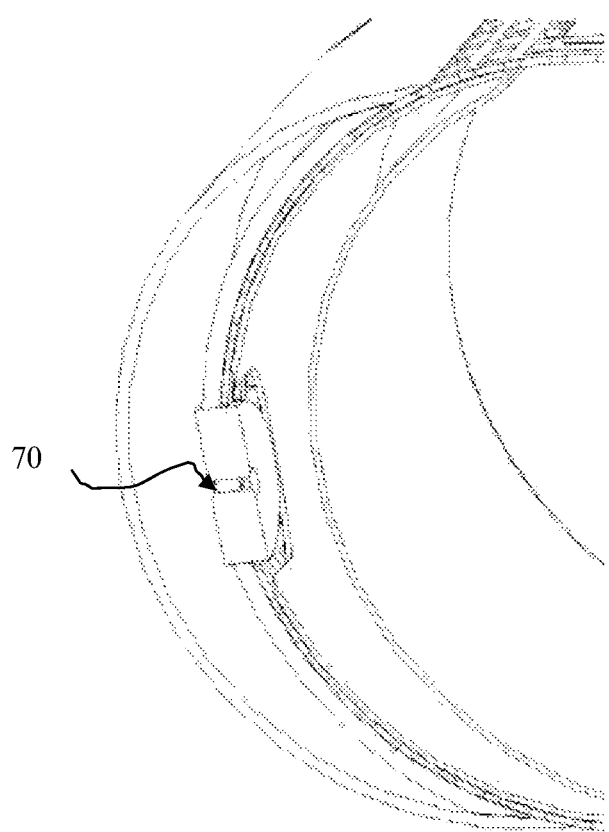
Figure 10:
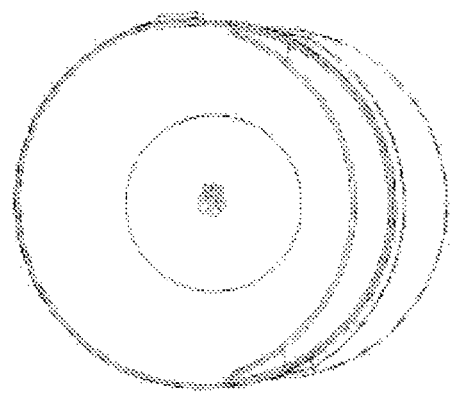
Figure 11:
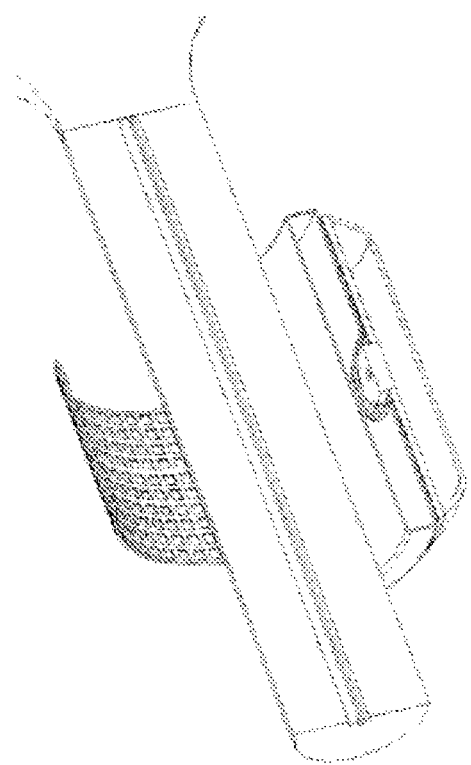

FIG. 7*a-c* illustrates the locking mechanism of the strap of a preferred embodiment of the present invention, placed around the urethra, in accordance with a preferred embodiment of the present invention;

FIG. 8*a-c* illustrates an embodiment of the present invention with the valve revealed, in accordance with a preferred embodiment of the present invention;

FIG. 9 illustrates a detail of the present invention showing the valve in situ in partial cross section, in accordance with a preferred embodiment of the present invention;

FIG. 10 illustrates a view of the collar, looking along the collar, in accordance with a preferred embodiment of the present invention;

FIG. 11 is a cross section view of the collar deployed upon the urethra.

Figure 12:
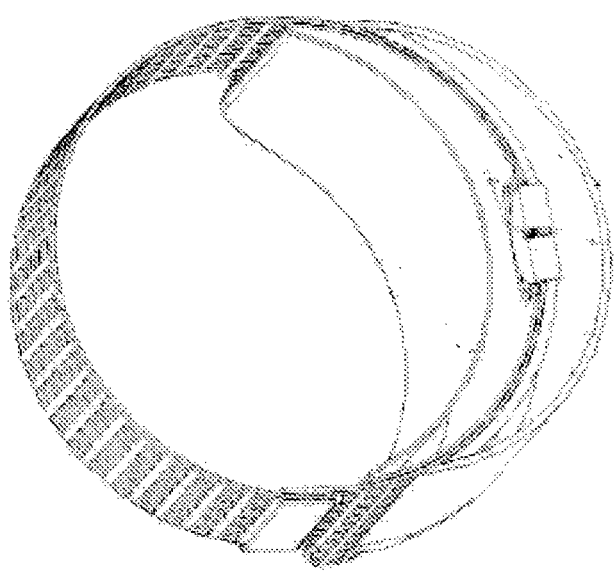
Figure 13:
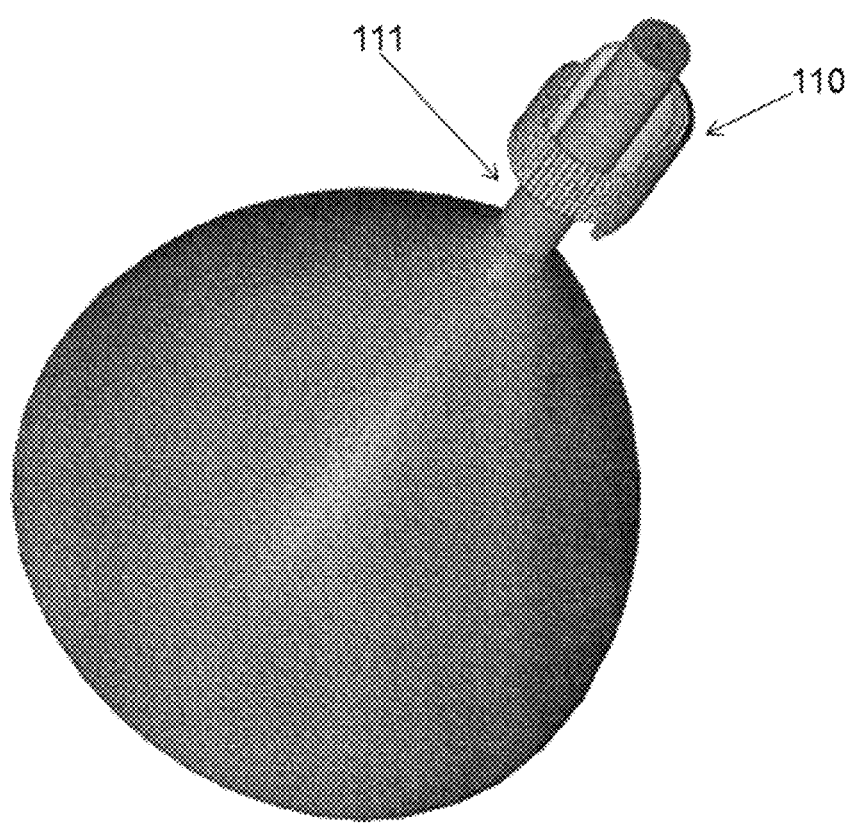
Figure 14:
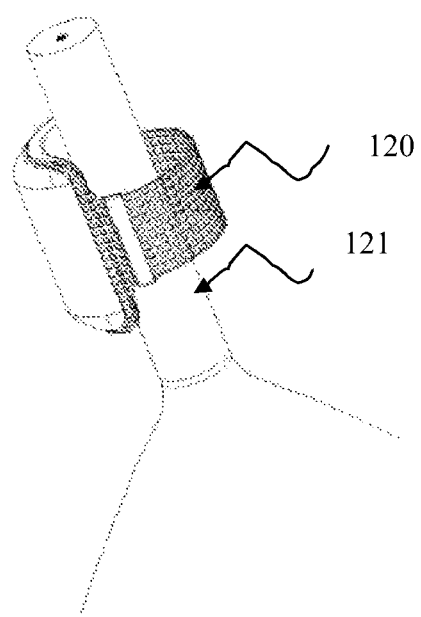

FIG. 12 is a top view of the collar, in accordance with a preferred embodiment of the present invention;

FIG. 13 illustrated the placing manner of the girth device upon the urethra, in accordance with a preferred embodiment of the present invention; and FIG. 14 is a top view of the placing manner of the girth device upon the urethra, in accordance with a preferred embodiment of the present invention;

DETAILED DESCRIPTION

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide device and method for controlling and preventing urinary incontinence. The device further provides internal organ support for a patient. The present invention is further directed to treat and prevent stress incontinence which characterized by urine leakage associated with increased abdominal pressure from laughing, sneezing, coughing, climbing stairs, or other physical stressors on the abdominal cavity and, thus, the bladder.

Figure 1A:
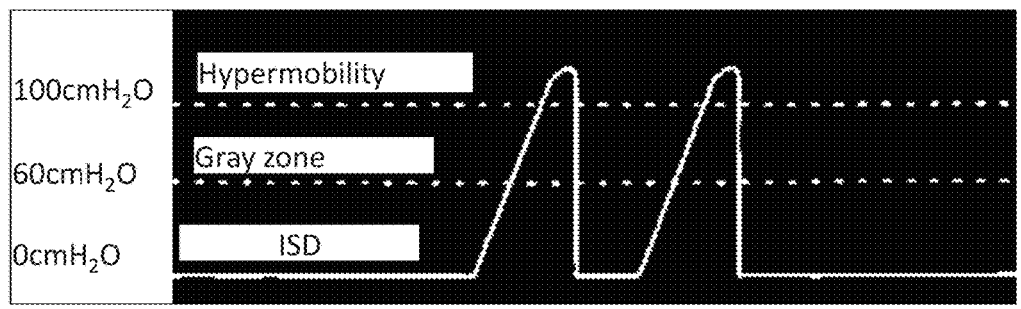
Figure 1B:
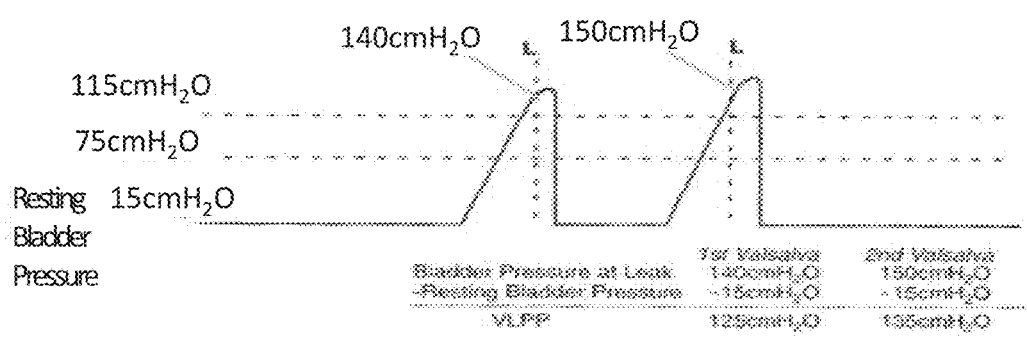
Figure 1B:
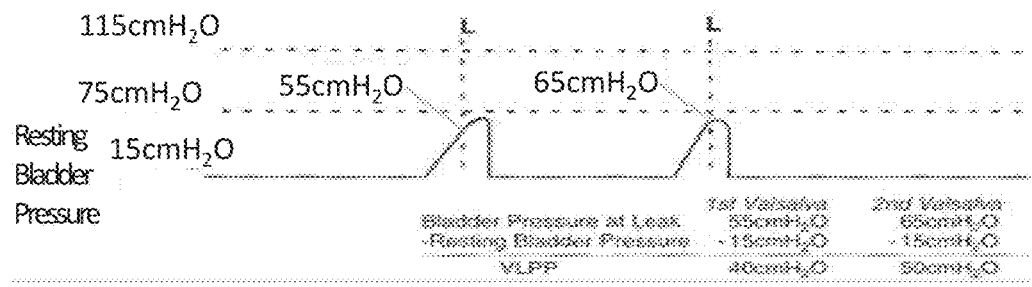

FIG. 1a-b presents a graph of the "Valsalva leak point pressure study" which is included in order to clarify the purpose of the present invention.

Leak point pressure is a measure of the interaction between detrusor pressure and urethral resistance. The Leak point pressure (LPP) is widely considered to be the best measure of urethral strength. The lower the urethral resistance for any given level of bladder compliance, the lower the leak point pressure and vice versa. In these circumstances, the sphincteric incontinence can be considered a "pop off valve" to protect the upper urinary tract at the expense of causing sphincteric incontinence. Many urologists and uro-gynecologists use abdominal leak point pressures below 60 cm $H_2O$ to define ISD or type III stress incontinence. A leak point pressure of less than 100 cm $H_2O$ is considered evidence of ISD by the FDA, although many specialists feel with values of 60-100 cm $H_2O$ in a "gray zone". In any case, patient history and other urodynamic findings need to be considered when determining the appropriate clinical management. It should be recognized that it is the vesical and not the abdominal pressure which provides the energy to drive urine across the sphincter and cause incontinence. Leak point pressures>40 cm $H_2O$ have been shown to cause hydronephrosis or vesicoureteral reflux. ("Urodynamic assessment: leak point pressures and urethral pressure profile", Women's Health & Education Center, Hospital Campus Medical Building)

Figure 2:
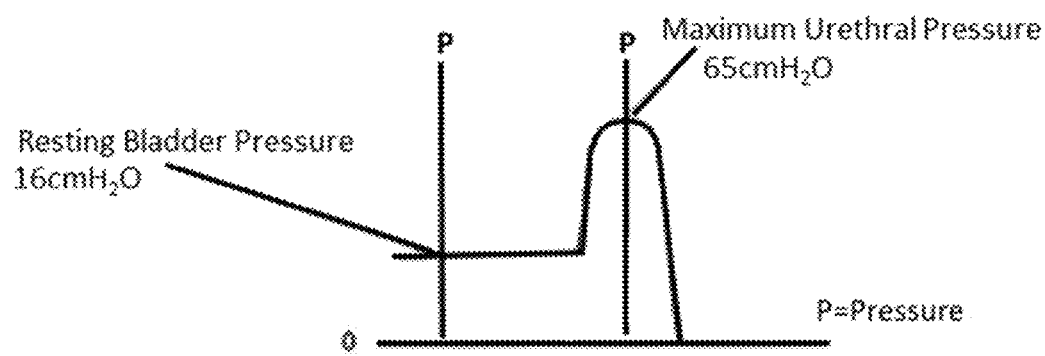

FIG. 2 presents a graph of the urethral pressure profile measurement:

A normal female Urethral Pressure Profile (UPP) is symmetric in shape, and asymmetry is generally caused by a faulty measurement technique. The values for normal urethral pressure have been noted in various studies to be decreasing with changes in vascularization that are inevitable with increasing age. There is trend towards lower urethral closure pressures and shorter functional length in stress incontinent patients than in patients who are stress continent. The appropriate way to report urethral function is to subtract out the influences of the bladder pressure (Pves). This is known as urethral closure pressure (Pclo) and is calculated as: Pclo=Pura−Pves. The maximum urethral closure pressure (MUCP) can be reported by subtracting the Pves pressure from the point of maximum urethral pressure (MUP). This formula is MUCP=MUP−Pves. Maximum urethral closure pressure over 30 cm $H_2O$ are considered normal, while an MUCP below 20 is considered an indication of urethral dysfunction or ISD. MUCP values of 20-30 are in a "gray zone," and should be considered along with other patient history and urodynamic information. ("Urodynamic assessment: leak point pressures and urethral pressure profile", Women's Health & Education Center, Hospital Campus Medical Building)

Figure 3:
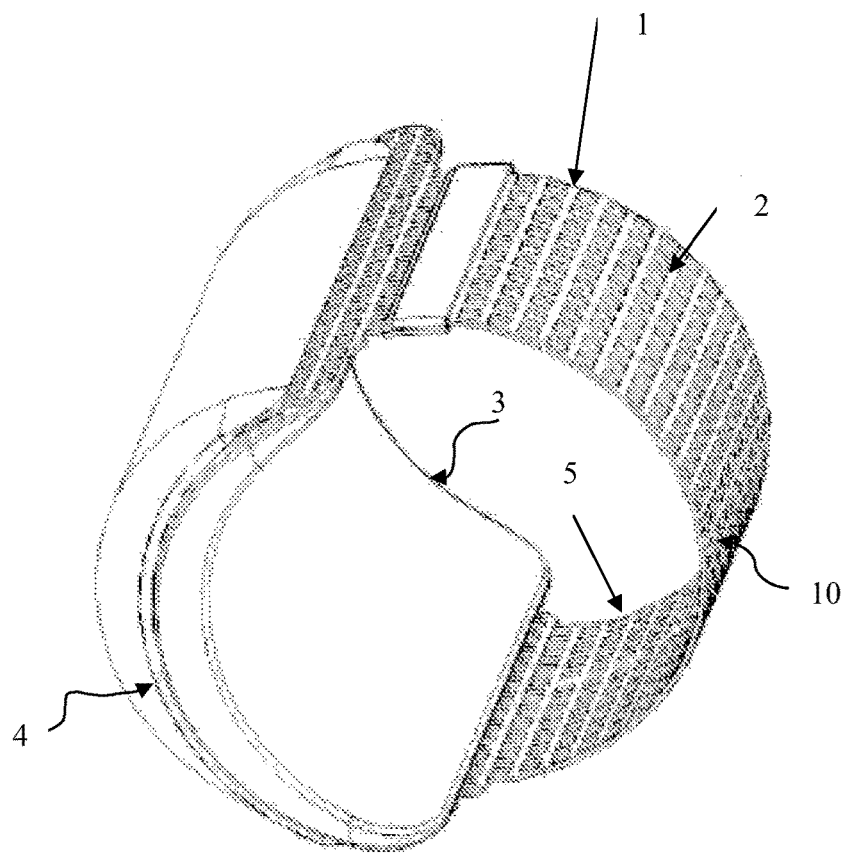

FIG. 3 presents an implantable girth device for controlling urinary incontinence comprising: (a) an adjustable resilient circumferential collar 1 for surrounding the urethra; said collar comprises: (i) a strap 10 for snugly embracing said urethra, said strap comprising an inner surface 5 and an outer surface 2, (ii) a first inflatable/deflatable expandable flexible elastic member 3 for limiting expansion of the lumen of said urethra affixed to portion of said inner surface 2 of said collar 10, (iii) a second inflatable/deflatable expandable non elastic reservoir 4 affixed to portion of said outer surface 2 of said collar 10; said expandable reservoir comprises a fluid, and (iv) a valve for fluidly communicating said first inflatable/deflatable expandable flexible elastic member 3 with said second inflatable/deflatable expandable non elastic reservoir 4.

The collar 1 pressure upon the urethra is increased or decreased with sensed urethra pressure such that when urethral pressure is exerted against the strap 10 the first expandable member 3 affixed to the strap is deflated by transferring the fluid through the valve to the second expandable reservoir 4 resulting in continence such that urine remains in the urethra for about 1.5 seconds. Furthermore, when urethral pressure decreases, the second expandable reservoir transfers the fluid to the first expandable member such that both the second expandable reservoir and the first expandable member approximately retains in their original shape.

Characteristic alterations of urethral pressure and length occur in patients with stress urinary incontinence. Patients with stress urinary incontinence demonstrated a decreased ability to voluntarily increase urethral pressure and also had evidence of pressure equalization on Valsalva maneuver and coughing.

The invention further discloses an implantable girth device for treating characteristic alterations of urethral pressure and length in patients with stress urinary incontinence. The girth device further treats patients with stress urinary incontinence which demonstrates a decreased ability to voluntarily increase urethral pressure and also had evidence of pressure equalization on Valsalva maneuver and coughing. The girth device comprises: (a) an adjustable resilient circumferential collar 1 for surrounding the urethra. The collar comprises: (i) a strap 10 for snugly embracing the urethra. The strap comprising an inner surface 5 and an outer surface 2,
(ii) a first inflatable/deflatable expandable flexible elastic member 3 for limiting expansion of the lumen of said urethra affixed to portion of said inner surface 5 of the collar, (iii) a second inflatable/deflatable expandable non elastic reservoir 4 affixed to portion of the outer surface 2 of the collar 10. The expandable reservoir 4 comprises a fluid; and (iv) a valve for fluidly communicating said first inflatable/deflatable expandable flexible elastic member 3 with said second inflatable/deflatable expandable non elastic reservoir 4.

The valve is configured to restrict fluid transfer between the first inflatable/deflatable expandable flexible elastic member 3 and the second inflatable/deflatable expandable non elastic reservoir 4 such that collar pressure upon the urethra is maintained between about 5 cms H$_2$O and about 20 cms H$_2$O for a about 1.5 secs. thereby limiting expansion of the urethral diameter beyond a predetermined diameter during intermittent abrupt high bladder and urethral pressure episodes of duration of about 0.5 secs.

The intermittent abrupt high bladder and urethral pressure episodes of duration of about 0.5 secs is about 150 cms. H$_2$O.

The girth device of the present invention is with the ability to adjust urethra and thus bladder pressure so that the collar exerts the minimum pressure necessary to maintain continence without causing urethral necrosis. The collar pressure is adjusted to compensate for increases in bladder pressure due to bladder fill, bladder spasm, voluntarily or involuntary tensing of the diaphragm or abdominal wall, or increased intra-abdominal pressure due to walking, sitting, coughing or laughing. When intra-abdominal pressure increases it is transmitted to both urethra and bladder equally, leaving the pressure differential unchanged, such that when voiding is performed changes in both of these pressure factors is occurred: urethral pressure is exerted against and bladder pressure rises.

Figure 4A:
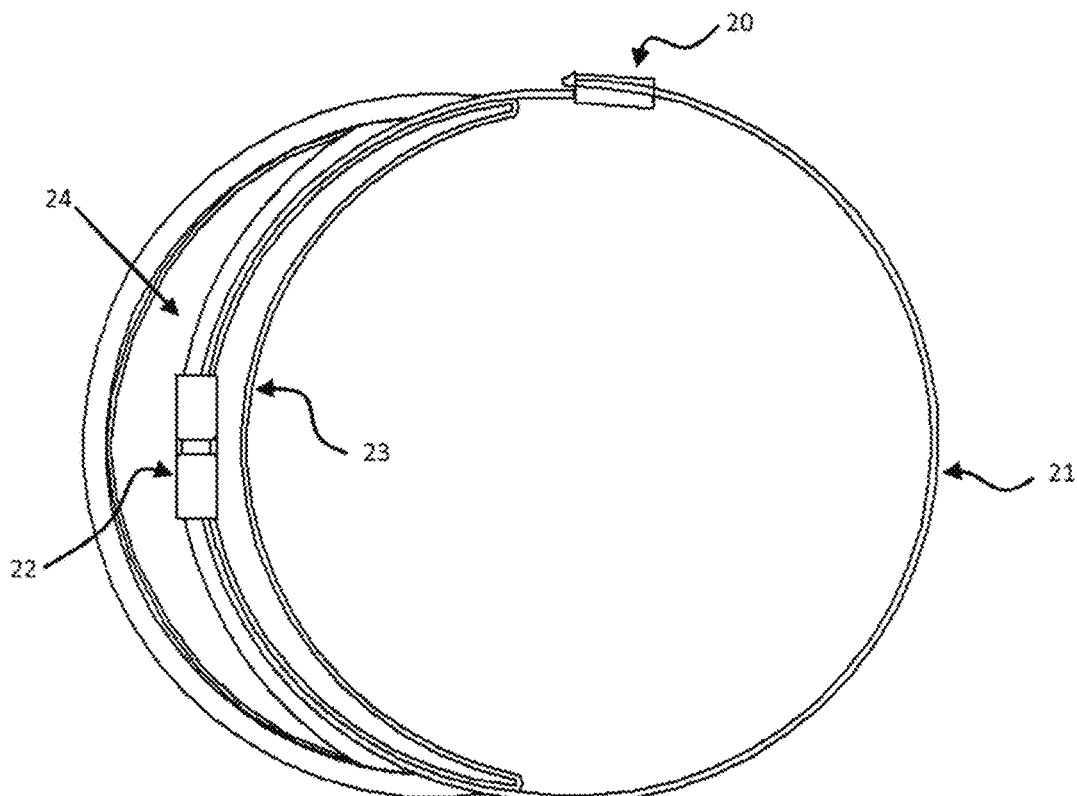

FIG. 4a is a top view of the girth device which comprises a collar having a strap 21, a buckle 20 located on the outer portion of the collar. The buckle is adapted for adjusting the diameter of the collar to the patient urethra diameter. The collar further comprises a (ii) a first inflatable/deflatable expandable flexible elastic member 23 for limiting expansion of the lumen of the urethra affixed to portion of the inner surface of the collar, (iii) a second inflatable/deflatable expandable non elastic reservoir 24 affixed to portion of the outer surface of the collar, and (iv) a valve 22 for fluidly communicating the first inflatable/deflatable expandable flexible elastic member 23 with the second inflatable/deflatable expandable non elastic reservoir 24. When a coughing or laughing are occurred that involve incontinence dripping or urine leakage. The valve has a predetermined diameter which maintains urethra pressure between about 5 cms H$_2$O and about 20 cms H$_2$O for a about 1.5 secs and thus preventing rapid changes in bladder pressure.

Figure 4B:
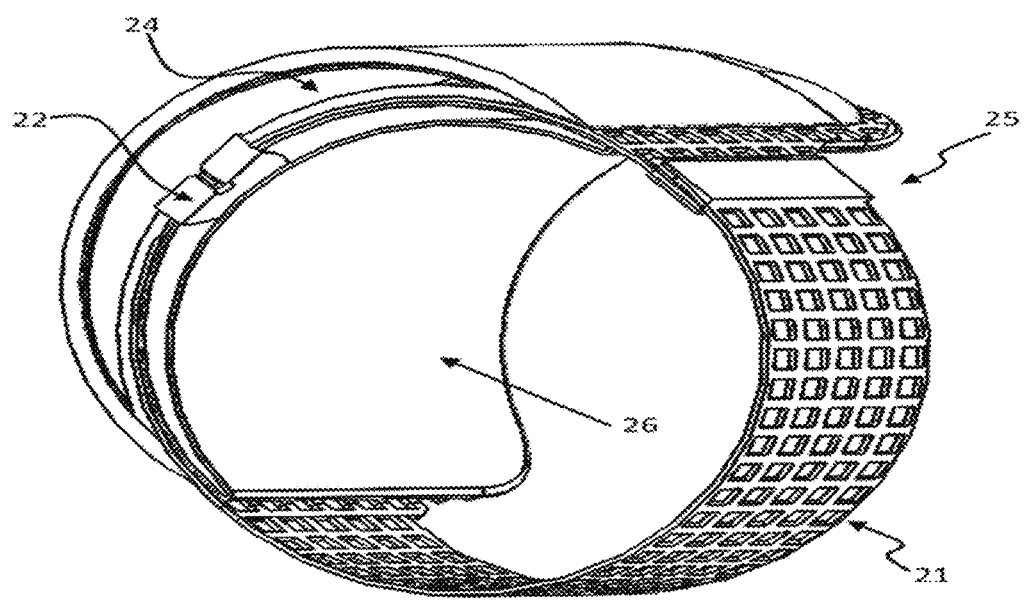
Figure 5:
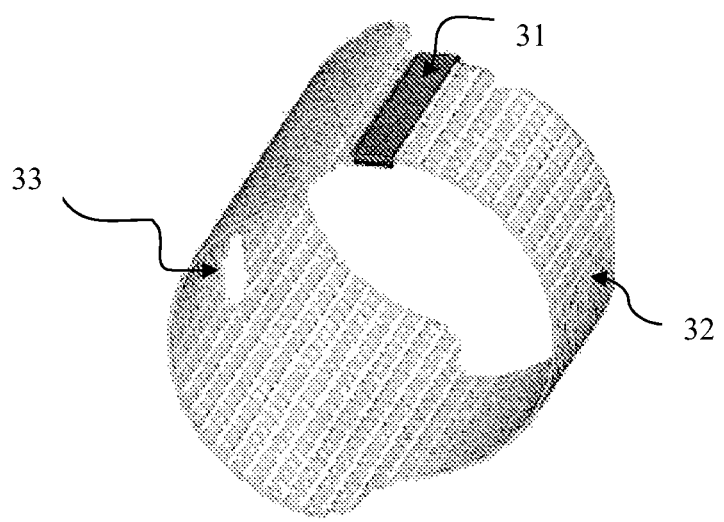
FIG. 5 is a side view of the girth device, in accordance with a preferred embodiment of the present invention.

FIG. 4b further illustrates a top-side view of the device of the present invention, width and thickness if the outer section and the inner section of the collar.

The collar may be of variety of lengths to accommodate different urethra size.

The collar is adapted for changing both the urethra and bladder pressure factors.

FIG. 5-8 illustrate the collar strap 32 having a belt like structure. The strap comprises a buckle 31 for adjusting the size and diameter of the collar to patient urethra. The strap is a biocompatible material made of a deformable material such as plastic. The strap includes a valve which has a bore hole 33 configuration for transferring the fluid.

The device is applied and placed in situ embracing the urethra. During the normal life activities of the patient, the collar device assumes 3 conformations:

The first conformation is defined by the inflated configuration of the first expandable member, adjacent to the outer wall of the urethra while the second expandable member is in its deflated configuration. Thus the urethra is limited by the collar at a predetermined diameter.

The second conformation is defined when an abrupt (0.5 secs) urethral pressure 150 cms. H$_2$O, such as that produced by an involuntary stress event (e.g. sneeze or laughter) is exerted against the strap. Because the first expandable member, affixed to the strap, is deflated only gradually (over about 1.5 secs) by the transferring of the fluid through the valve to the second expandable reservoir, the strap continues to confine the diameter of the urethra at the predetermined diameter, preventing urine leakage.

The third position is formed when urethral pressure decreases, or returns to normal. The second expandable reservoir transfers the fluid by return to the first expandable member, (taking 1.5 secs) such that both the second expandable reservoir and the first expandable member are restored to their original shape (the first expandable member is in its inflated configuration and the second expandable reservoir is in its deflated configuration).

Figure 6:
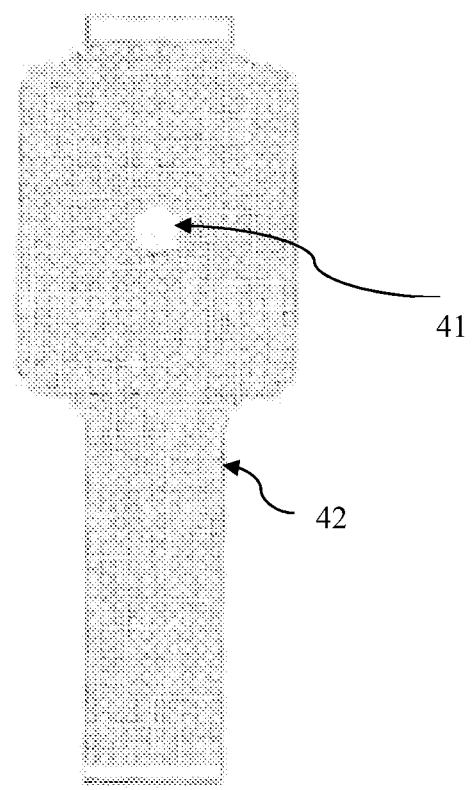
FIG. 6 illustrates the strap (without expandable members) in its open configuration, in accordance with a preferred embodiment of the present invention.

FIG. 6 illustrates the open configuration of the strap 42 having a bore hole 41 which allows fluid flow. In FIG. 4 the collar comprises at least one broad strap portion and at least one narrow strap portion. The strap may further have a uniform width. It is further illustrates that at least one portion of the strap may have a mesh like structure.

FIG. 7a-c presents the closed configuration, as shown in FIG. 7c, and the open configuration, as shown in FIG. 7a. FIG. 7 further illustrates the steps 7a-c for closing the strap upon the urethra by using the buckle 50 as a locking element. The strap is gird in a snugly embracing manner such that it increases sphincter fluid pressure only for the length of the spasm, thereby causing no threat of tissue necrosis. The invented girth device therefore can provide continence during bladder pressure peaks without causing necrosis of the urethral tissue. The strap has a belt like structure having an engaging mechanism such that it may be adjusted to different urethra size. The engaging mechanism allows to maintain the pressure on the urethra and to achieve continence.

The collar balance between urethral closure and detrusor muscle activity.

The strap's circumference can be adjusted as needed for comfort by selecting an appropriate location for closing the buckle. Alternate closing mechanisms, such as velcro, snaps, zippers, tension clip or any fasten manner known in the art may further be adapted.

Unfastening of the strap from its circular closed position is easily achieved by lifting the edge 51. FIG. 7 further illustrates the maneuvering manner of the buckle 50 of the strap in a convenient direction either for tightening the device or for loosening or removing it.

FIG. 8a is a top view of the girth device of the present invention.

FIG. 8b is a side view of the girth device of the present invention which further illustrates the difference in thickness of the strap and the expandable members. As illustrates both of the expandable members are affixed to the strap of the device. The expandable members attached to the strap are adapted to be deployed around the urethra. The expandable members area attached to a portion of the strap or may further be attached to all the strap length.

The first expandable member can be a natural or synthetic material which has the ability to quickly recover or return to approximately its original shape and/or dimension or position after being bent, stretched or compressed. Such change to the expandable member can be created by changes in the intra-abdominal pressure. The first expandable member can be filled with fluid, or the fluid pressure can be reset, after implantation without necessitating a surgical procedure. The first expandable member is a biocompatible material made of an elastic material such as nylon.

The second expandable member is made of un elastic material but with the ability to be expanded by a fluid.

The deflation of the first expandable member lower the pressure of the collar upon the urethra therefore resulting release of urine.

The first inflatable/deflatable expandable flexible elastic member and the second inflatable/deflatable expandable non elastic reservoir act as double-expandable members.

The collar is inserted in the urethra and is held therein by the double-expandable members. The double-expandable members is filled or emptied via a valve having a connecting tunnel which connects the two expandable members FIG. 8c illustrates the valve having a connecting tunnel 60 which connects the two expandable members. The valve tunnel allows fluid to pass between the expandable members. The fluid is selected from a group consisting of viscous fluid or water based fluid. The first inflatable/deflatable expandable flexible elastic member may further be adjusted to the patient urethra pressure in parallel to her pelvic floor muscle status. The adjustment is performed by extracting fluid or by infusing additional fluid to the inflatable/deflatable expandable member using a syringe or the like without damaging the device.

The valve has a predetermined diameter and structure which allows fluid flow passage there through. The fluid flow from first expandable member to second expandable reservoir takes 1.5 seconds, allowing the collar to control the flow of urine by activating pressure on the urethra such that when a urine leakage is predicted to occur the collar retain the urine within the urethra for 1.5 seconds. Therefore ameliorating incontinence.

The girth device of the present invention comprises a valve which is adjustable and controllable valve adjusted to the user urethra pressure parameters.

The present invention further provides an orifice for fluidly communicating a first inflatable/deflatable expandable flexible elastic member with a second inflatable/deflatable expandable non elastic reservoir of an implantable girth device.

The girth device is for controlling urinary incontinence.

The orifice is a valve configured to restrict fluid transfer between the expandable first inflatable/deflatable expandable flexible elastic member and second inflatable/deflatable expandable non elastic reservoir such that girth device pressure upon the urethra is maintained between about 5 cms $H_2O$ and about 20 cms $H_2O$ for a about 1.5 secs. thereby limiting expansion of the urethral diameter beyond a predetermined diameter during intermittent abrupt high bladder and urethral pressure episodes of duration of about 0.5 secs The orifice structure is selected from a group consisting of valve, tube-like, passage like, orifice annular, pipe, needle valve, hole, nozzle or any structure designed to control the direction or characteristics of a fluid flow.

FIG. 9 illustrate a cross section view of the valve 70 having a tunnel structure for fluidly communicating of the first inflatable/deflatable expandable flexible elastic member with the second inflatable/deflatable expandable non elastic reservoir.

FIG. 10 present a top view of the collar. FIG. 10. illustrates the collar configuration and its hollow structure allowing it to be employed and dressed upon the urethra.

The collar is made from a biocompatible material in a mesh like structure allowing it to join with the patient tissue. the mesh like structure may be applied on a portion of the collar or all over its length. The collar may further be made of a smooth material such that a portion may be extracted from the patient body.

FIG. 11 is a cross section view of the collar employed upon the urethra.

The collar is applied to the urethra in its open configuration and then closed upon the urethra as a belt like close manner, such that the collar is "buckling up" the urethra. The collar is adapted to remain as a long residence device upon the urethra. it consists of a flexible but rigid biocompatible material which does not damage or harm the body tissue. FIG. 11 further illustrates the cross section of the valve located between the expandable members.

FIG. 12 presents a top view of the collar while illustrating the cross section view of the valve for fluidly communicating of the first inflatable/deflatable expandable flexible elastic 4 member with the second inflatable/deflatable expandable non elastic reservoir 5. The valve comprises a bore hole which has a tunnel like structure. The valve may have a diameter correlated to the required pressure and required duration in order to prevent leakage of urine from the urethra. In the other hand the fluid may have viscous properties such that the appropriate conditions of pressure and duration of fluid transfer from the first expandable member and the second expandable reservoir and vice versa.

The fluid and the valve diameter are adjusted in a manner which will provide and maintain pressure upon the urethra between about 5 cms $H_2O$ and about 20 cms $H_2O$ for about 1.5 secs., thereby limiting expansion of the urethral diameter beyond a predetermined diameter during intermittent abrupt high bladder and urethral pressure episodes of duration of about 0.5 secs.

FIG. 13 illustrates the manner which the girth device 110 is applied upon the urethra 111. As illustrated, the adjustable resilient circumferential collar surrounds the urethra such that the collar portion having the expandable members embraces the urethra in a manner which limits the expansion of the urethral diameter beyond a predetermined diameter.

FIG. 14 shows the girth device 120 of the present invention, surrounding a portion of the urethra 121. The collar is implanted such that it surrounds the wall of the urethra, thereby directly sensing and controlling urethra expansion pressure.

The present invention further presents a method of controlling urinary incontinence comprising the steps of: (a) providing an urethra implanted device for treating urinary incontinence comprising: (i) an adjustable resilient circumferential collar 10 for surrounding the urethra; the collar comprises: (a) a strap for snugly embracing the urethra, the strap comprising an inner surface and an outer surface, (b) a first inflatable/deflatable expandable flexible elastic member 3 for limiting expansion of the lumen of the urethra affixed to portion of the inner surface 2 of the collar; (c) a second inflatable/deflatable expandable non elastic reservoir 4 affixed to portion of the outer surface 1 of the collar 10; the expandable reservoir comprises a fluid, and (d) a valve for fluidly communicating the first inflatable/deflatable expandable flexible elastic member with the second inflatable/deflatable expandable non elastic reservoir;

b) placing the urethra implanted device upon the urethra; and (c) adjusting and securing the collar strap for surrounding the urethra in a manner for occluding the flow of urine from the urethra and to allow the flow of urine from the urethra. Further more the collar pressure upon the urethra is increased or decreased with sensed urethra pressure such that when urethral pressure is exerted against the strap the first expandable member affixed to the strap is deflated by transferring the fluid through the valve to the second expandable reservoir resulting in continence such that urine remains in the bladder for about 1.5 seconds; further wherein when urethral pressure decreases, the second expandable reservoir transfers the fluid to the first expandable member such that both the second expandable reservoir and the first expandable member are approximately resuming their original shape.

The present invention further presents a method of controlling urinary incontinence comprising the steps of: (a) providing an urethra implanted device for treating urinary incontinence comprising: (i) an adjustable resilient circumferential collar 10 for surrounding the urethra; the collar comprises: (a) a strap for snugly embracing the urethra, the strap comprising an inner surface and an outer surface, (b) a first inflatable/deflatable expandable flexible elastic member 3 for limiting expansion of the lumen of the urethra affixed to portion of the inner surface 2 of the collar; (c) a second inflatable/deflatable expandable non elastic reservoir 4 affixed to portion of the outer surface 1 of the collar 10; the expandable reservoir comprises a fluid, and, (d) a valve for fluidly communicating the first inflatable/deflatable expandable flexible elastic member with the second inflatable/deflatable expandable non elastic reservoir. The valve is configured to restrict fluid transfer between the expandable first inflatable/deflatable expandable flexible elastic 4 member and second inflatable/deflatable expandable non elastic reservoir 5 such that collar pressure upon the urethra is maintained between about 5 cms $H_2O$ and about 20 cms $H_2O$ for a about 1.5 secs. thereby limiting expansion of the urethral diameter beyond a predetermined diameter during intermittent abrupt high bladder and urethral pressure episodes of duration of about 0.5 secs.
(b) placing the urethra implanted device upon the urethra; and (c) adjusting and securing the collar strap for surrounding the urethra.

In another embodiment of the present invention, the valve is configured to restrict fluid transfer between the expandable first inflatable/deflatable expandable flexible elastic 4 member and second inflatable/deflatable expandable non elastic reservoir 5 such that collar pressure upon the urethra is maintained between about 5 cms $H_2O$ and about 20 cms $H_2O$ for a about 1.5 secs. thereby limiting expansion of the urethral diameter beyond a predetermined diameter during intermittent abrupt high bladder and urethral pressure episodes of duration of about 0.5 secs.

In another embodiment of the invention the method as described above, wherein the intermittent abrupt high bladder and urethral pressure episodes of duration of about 0.5 secs is about 150 cms. $H_2O$.

In another embodiment of the invention the method as described above, further comprises the step of closing the strap around the urethra in a generally circular shape using a buckle.

In another embodiment of the invention the method as described above, wherein the collar has an open configuration and a close configuration.

In another embodiment of the invention the method as described above, wherein the inserting the urethra implanted device in been performed in a manner such as an open position of the strap or a closed position of the strap In another embodiment of the invention the method as described above, wherein the collar is adapted for changing both the urethra and bladder pressure factors.

In another embodiment of the invention the method as described above, wherein the first expandable member is filled with fluid, or the fluid pressure can be reset, after implantation without necessitating a surgical procedure.

In another embodiment of the invention the method as described above, wherein the first expandable member is made of an elastic material which has biocompatible characters.

In another embodiment of the invention the method as described above, wherein the second expandable member is made of un elastic material which has biocompatible characters.

In another embodiment of the invention the method as described above, wherein the collar may be of different sizes to accommodate different urethra size.

In another embodiment of the invention the method as described above, wherein the strap has a belt like structure such that it may be adjusted to different urethra size.

In another embodiment of the invention the method as described above, wherein the strap has a resilient circumferential shape having a buckle for opening and closing the strap.

In another embodiment of the invention the method as described above, wherein the collar balance between urethral closure and detrusor muscle activity In another embodiment of the invention the method as described above, wherein the fluid consists of viscous or water based fluids.

In another embodiment of the invention the method as described above, wherein the valve for fluidly communicating has a diameter such that fluid transfer between the expandable first inflatable/deflatable expandable flexible elastic 4 member and the second inflatable/deflatable expandable non elastic reservoir takes about 1.5 secs.

In another embodiment of the invention the method as described above, wherein transferring the fluid from first expandable member to second expandable reservoir takes 1.5 seconds, allowing the collar to control the flow of urine by activating pressure on the urethra.

In another embodiment of the invention the method as described above, wherein deflation of the first expandable member lower the pressure of the collar upon the urethra therefore resulting release of urine.

In another embodiment of the invention the method as described above, wherein the valve has an inner lumen shape for fluidly communicating of the first inflatable/deflatable expandable flexible elastic member with the second inflatable/deflatable expandable non elastic reservoir.

In another embodiment of the invention the method as described above, wherein the collar comprises a broad strap portion and a narrow strap portion In another embodiment of the invention the method as described above, wherein the strap has a mesh like structure.

The present invention is based on the abdominal leak point pressure measurements.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An implantable girth control device for controlling urinary incontinence comprising:
   an adjustable resilient circumferential collar for surrounding a urethra; said collar comprises:
   a. a strap for snugly embracing said urethra, said strap comprising an inner surface and an outer surface;
   b. a first inflatable/deflatable expandable member for limiting expansion of a lumen of said urethra, said first member affixed to a portion of said inner surface of said collar; said first member comprises a fluid;
   c. a second inflatable/deflatable expandable member providing a reservoir affixed to a portion of said outer surface of said collar; and
   d. a valve for fluidly communicating said first member with said second member;
   e. wherein said valve is configured to control a collar pressure applied onto the urethra and responsive to changes in urethral pressure wherein said valve facilitates fluid transfer between said first member and said second member based on said changes in urethral pressure to control the girth of said device around the urethra and therein said applied collar pressure.

2. The device of claim 1 configured to be responsive to an increase in said urethral pressure, wherein said valve is configured to facilitate fluid transfer between said first member and said second member when said urethral pressure is exerted against said first member resulting in continence.

3. The device of claim 2, wherein said fluid transfer via said valve is configured for the urine to remain in said urethra for 1.5 seconds, therein urethral diameter expansion is limited for a period of 1.5 seconds.

4. The device of claim 2 further configured to be responsive to a decrease in said urethral pressure following an instance of said urethral pressure increase, wherein said valve is configured to transfer said fluid from said second member to said first member to allow both said second member and said first member are configured to assume their original shape.

5. The device according to claim 1, wherein said collar pressure applied upon said urethra is configured to be between 5 cm $H_2O$ and 20 cm $H_2O$.

6. The device according to claim 5, wherein said collar pressure applied onto the urethra is configured to limit urethral diameter expansion to a predetermined diameter during episodes of said urethral pressure changes and intermittent abrupt high bladder pressure, said episodes having a duration of 0.5 seconds.

7. The device of claim 1, wherein said valve is selected from a group consisting of: valve, tube, passage, annular orifice, pipe, needle valve, hole, nozzle, tunnel, or any structure designed to control a fluid flow direction or characteristics of a fluid flow therethrough.

8. The device according to claim 1, wherein said first member is filled with said fluid defining a fluid pressure within said first member, and wherein said fluid pressure is adjustable after implantation, wherein said adjustment is provided without necessitating a surgical procedure.

9. The device according to claim 8, wherein said fluid pressure of said first member is configurable according to urethral native pressure.

10. The device according to claim 1, wherein said strap has a buckle for sizing and adjusting said strap to fit different urethral sizes.

11. The device according to claim 1, wherein said fluid is selected from a group consisting of a viscous fluid or a water based fluid.

12. The device of claim 11, wherein said fluid is a viscous fluid and wherein said fluid's viscosity is controlled to control flow between said first member and said second member.

13. The device of claim 12, wherein said viscous fluid's properties are configured to control flow parameters, including at least one of: a fluid pressure at which said fluid transfer is initiated or duration of said fluid transfer.

14. The device according to claim 1, wherein said valve provides a flow channel having a predetermined diameter and structure which allows fluid flow passage there through.

15. The device of claim 1, wherein said valve is configured to restrict fluid transfer between said first member and said second member in order to maintain said collar pressure.

16. The device of claim 1, wherein said valve defines a flow channel for fluidly communicating said first member with said second member; wherein the flow channel parameters are configured according to said collar pressure and a fluid transfer duration required to provide urethral continence therein preventing leakage of urine from the urethra.

17. The device of claim 16, wherein said flow channel parameters is flow channel diameter.

18. The device according to claim 16, wherein said flow channel parameters are further configured according to said fluid's properties.

19. A method of controlling urinary incontinence, the method comprising:
   a. providing an implantable girth control device for controlling urinary incontinence, the device having an adjustable resilient circumferential collar for surrounding a urethra; said collar including:
      i. a strap for snugly embracing said urethra, said strap comprising an inner surface and an outer surface;
      ii. a first inflatable/deflatable expandable member for limiting expansion of a lumen of said urethra, said first member affixed to a portion of said inner surface of said collar; said first member comprises a fluid;
      iii. a second inflatable/deflatable expandable member providing a reservoir affixed to a portion of said outer surface of said collar; and
      iv. a valve for fluidly communicating said first member with said second member;
      v. wherein said valve is configured to control a collar pressure applied onto the urethra and responsive to changes in urethral pressure wherein said valve facilitates fluid transfer between said first member and said second member based on said changes in urethral pressure to control the girth of said device around the urethra and therein said applied collar pressure;
   b. associating said device upon a urethra; and
   c. adjusting and securing said device to surround the urethra, wherein the external surface of the urethra is in contact with the inner surface of said device along said first member, wherein said device is responsive to changes in urethral pressure, and wherein said device is configured to transfer a fluid between said first member and said second member through said valve.

20. The method of claim 19, wherein said device is introduced to surround the urethra in a minimally invasive manner.

21. The method according of claim 19, further comprising adjusting a volume of a fluid disposed within said first member and said second member to adjust a collar pressure exerted on the urethra to be between 5 cm $H_2O$ and 20 cm $H_2O$.

22. The method of claim 21, wherein adjusting the volume of fluid disposed within said first member is resetable and/or adjustable, after implantation without necessitating surgical procedure.

23. The method of claim 21, wherein a minimal collar pressure necessary to maintain continence without causing urethral necrosis is exerted onto the urethra by adjusting the pressure applied by said device onto the urethra.

24. The method of claim 19, wherein said valve provides a flow channel having a controllable diameter and wherein said diameter is determined and set during implantation.

25. The method of claim 19, wherein said fluid and said fluid's properties are determined during implantation, and wherein said fluid is selected from the group consisting of: a viscous fluid or a water based fluid.

26. The method of claim 25, wherein said fluid is a viscous fluid, and wherein said fluid's viscosity is controlled to control flow between said first member and said second member, and wherein said viscous fluid's properties are configured to control flow parameters including at least one of: pressure at which said fluid transfer is initiated or duration of said fluid transfer.

* * * * *